United States Patent
Kim et al.

(10) Patent No.: US 11,434,271 B2
(45) Date of Patent: Sep. 6, 2022

(54) METHOD FOR PREPARING PHYSIOLOGICALLY ACTIVE POLYPEPTIDE COMPLEX

(71) Applicant: HANMI SCIENCE CO., LTD, Hwaseong-si (KR)

(72) Inventors: Dae Jin Kim, Hwaseong-si (KR); Myung Hyun Jang, Seoul (KR); Seung Su Kim, Seoul (KR); Jong Soo Lee, Seongnam-si (KR); Jae Hyuk Choi, Seoul (KR); Se Chang Kwon, Seoul (KR)

(73) Assignee: HANMI SCIENCE CO., LTD., Hwaseong-si (KR)

( * ) Notice: Subject to any disclaimer, the term of this patent is extended or adjusted under 35 U.S.C. 154(b) by 0 days.

(21) Appl. No.: 14/356,054

(22) PCT Filed: Nov. 2, 2012

(86) PCT No.: PCT/KR2012/009186
§ 371 (c)(1),
(2) Date: May 2, 2014

(87) PCT Pub. No.: WO2013/066106
PCT Pub. Date: May 10, 2013

(65) Prior Publication Data
US 2014/0296475 A1    Oct. 2, 2014

(30) Foreign Application Priority Data
Nov. 4, 2011  (KR) ................. 10-2011-0114828

(51) Int. Cl.
*C07K 14/62* (2006.01)
*C07K 1/107* (2006.01)
(Continued)

(52) U.S. Cl.
CPC .............. *C07K 14/62* (2013.01); *A61K 47/60* (2017.08); *C07K 1/1077* (2013.01); *C07K 17/08* (2013.01);
(Continued)

(58) Field of Classification Search
CPC ...... C07K 14/62; C07K 17/08; C07K 1/1077; C07K 2319/30; C07K 2319/31
See application file for complete search history.

(56) References Cited

U.S. PATENT DOCUMENTS 6,756,480 B2    6/2004  Kostenuik et al.
6,924,264 B1    8/2005  Prickett et al.
(Continued)

FOREIGN PATENT DOCUMENTS

CN    1777440 A    5/2006
CN    102112493 A    6/2011
(Continued)

OTHER PUBLICATIONS

Koonin et al., Chapter 2 Evolutionary Concept in Genetics and Genomics, Sequence—Evolution—Function: Computational Approaches in Comparative Genomics. Boston: Kluwer Academic; 2003; NCBI Bookshelf; attached as pdf, 25 pages (Year: 2003).*
(Continued)

*Primary Examiner* — Randall L Beane
(74) *Attorney, Agent, or Firm* — Sughrue Mion, PLLC

(57) ABSTRACT

A method for preparing a conjugate of a physiologically active polypeptide and a non-peptide polymer by linking physiologically active polypeptide with non-peptide polymer through a covalent bond using an organic solvent is provided. A method for preparing a physiologically active polypeptide complex by linking the conjugate with a carrier is provided. The complex shows improved in vivo duration and stability of the physiologically active polypeptide. The
(Continued)

method can prepare the conjugate at a lower production cost, and the resulting conjugate shows an extension of in vivo activity at a relatively high level and significantly increase in the blood half-life.

9 Claims, 6 Drawing Sheets

Specification includes a Sequence Listing.

(51) Int. Cl.
  *C07K 17/08* (2006.01)
  *A61K 47/60* (2017.01)
(52) U.S. Cl.
  CPC ...... *C07K 2319/30* (2013.01); *C07K 2319/31* (2013.01)

(56) References Cited

U.S. PATENT DOCUMENTS

| | | | |
|---|---|---|---|
| 7,256,258 B2* | 8/2007 | Piquet | A61K 47/48215 530/335 |
| 7,737,260 B2 | 6/2010 | Kim et al. | |
| 8,163,889 B2 | 4/2012 | Kim et al. | |
| 8,263,084 B2 | 9/2012 | Song et al. | |
| 8,476,230 B2* | 7/2013 | Song | C07K 14/605 424/195.11 |
| 8,829,163 B2 | 9/2014 | Bae et al. | |
| 8,895,281 B2* | 11/2014 | Song | A61K 47/48215 435/183 |
| 9,061,072 B2 | 6/2015 | Hong et al. | |
| 9,072,794 B2 | 7/2015 | Woo et al. | |
| 9,186,415 B2* | 11/2015 | Kim | A61K 47/48369 |
| 9,421,244 B2 | 8/2016 | Kim et al. | |
| 9,492,507 B2 | 11/2016 | Song et al. | |
| 9,504,757 B2 | 11/2016 | Kim et al. | |
| 9,597,378 B2 | 3/2017 | Kim et al. | |
| 9,636,420 B2 | 5/2017 | Song et al. | |
| 9,669,105 B2 | 6/2017 | Im et al. | |
| 9,724,420 B2 | 8/2017 | Kim et al. | |
| 9,731,031 B2 | 8/2017 | Jung et al. | |
| 9,750,820 B2 | 9/2017 | Jung et al. | |
| 9,789,202 B2 | 10/2017 | Jung et al. | |
| 9,801,950 B2 | 10/2017 | Kim et al. | |
| 9,833,516 B2 | 12/2017 | Lim et al. | |
| 9,867,777 B2 | 1/2018 | Lee et al. | |
| 9,901,621 B2 | 2/2018 | Jung et al. | |
| 9,981,017 B2 | 5/2018 | Song et al. | |
| 10,046,061 B2 | 8/2018 | Jang et al. | |
| 10,071,171 B2 | 9/2018 | Song et al. | |
| 10,660,940 B2 | 5/2020 | Jang et al. | |
| 2003/0228652 A1 | 12/2003 | Radhakrishnan et al. | |
| 2004/0180054 A1 | 9/2004 | Kim et al. | |
| 2006/0269533 A1 | 11/2006 | Molin et al. | |
| 2006/0269553 A1* | 11/2006 | Kim | A61K 47/48415 424/155.1 |
| 2007/0083006 A1* | 4/2007 | Hinds | A61K 47/48215 525/54.1 |
| 2009/0053246 A1* | 2/2009 | Kim | A61K 47/48415 424/178.1 |
| 2009/0252703 A1* | 10/2009 | Gegg, Jr. | C07K 1/1077 424/85.2 |
| 2010/0105869 A1 | 4/2010 | Kim et al. | |
| 2010/0255014 A1 | 10/2010 | Kim et al. | |
| 2011/0200623 A1* | 8/2011 | Song | A61K 47/48215 424/178.1 |
| 2013/0028918 A1 | 1/2013 | Song et al. | |
| 2013/0288333 A1 | 10/2013 | Kim et al. | |
| 2014/0005361 A1 | 1/2014 | Gillies et al. | |
| 2014/0120120 A1 | 5/2014 | Woo et al. | |
| 2014/0377290 A1 | 12/2014 | Kim et al. | |
| 2015/0025227 A1 | 1/2015 | Jung et al. | |
| 2015/0118255 A1 | 4/2015 | Lim et al. | |
| 2015/0196643 A1 | 7/2015 | Lim et al. | |
| 2015/0299247 A1 | 10/2015 | Jang et al. | |
| 2015/0299282 A1 | 10/2015 | Kim et al. | |
| 2016/0000931 A1 | 1/2016 | Jang et al. | |
| 2016/0008483 A1 | 1/2016 | Hwang et al. | |
| 2016/0008484 A1 | 1/2016 | Jang et al. | |
| 2016/0051696 A1 | 2/2016 | Song et al. | |
| 2016/0152684 A1 | 6/2016 | Hwang et al. | |
| 2016/0158378 A1 | 6/2016 | Park et al. | |
| 2016/0213789 A1 | 7/2016 | Rim et al. | |
| 2017/0100488 A1 | 4/2017 | Park et al. | |
| 2017/0196943 A1 | 7/2017 | Jung et al. | |
| 2017/0340753 A1 | 11/2017 | Jung et al. | |
| 2017/0360939 A1 | 12/2017 | Kim et al. | |
| 2018/0015175 A1 | 1/2018 | Kim et al. | |
| 2019/0083579 A1 | 3/2019 | Woo et al. | |
| 2019/0119347 A1 | 4/2019 | Kim et al. | |
| 2019/0153060 A1 | 5/2019 | Oh et al. | |
| 2019/0269779 A1 | 9/2019 | Kim et al. | |
| 2019/0269787 A1 | 9/2019 | Jung et al. | |

FOREIGN PATENT DOCUMENTS

| | | |
|---|---|---|
| CN | 103509118 A | 1/2014 |
| EP | 0 330 227 | 8/1989 |
| EP | 1682581 A1 | 7/2006 |
| HU | 213 019 B | 1/1997 |
| JP | 2006-520384 | 9/2006 |
| JP | 2007531513 A | 11/2007 |
| JP | 2008-538200 A | 10/2008 |
| JP | 2008-543916 A | 12/2008 |
| JP | 2010515677 A | 5/2010 |
| JP | 2011-505355 A | 2/2011 |
| JP | 2011-529046 A | 12/2011 |
| JP | 2013-500375 A | 1/2013 |
| JP | 2013537525 A | 10/2013 |
| KR | 1020040081378 A | 9/2004 |
| KR | 1020050047032 A | 5/2005 |
| KR | 10-0775343 A | 11/2007 |
| KR | 10-0824505 B1 | 4/2008 |
| KR | 10-2008-0064750 A | 7/2008 |
| KR | 10-2009-0056796 A | 6/2009 |
| KR | 1020100010919 A | 2/2010 |
| KR | 1020100105494 A | 9/2010 |
| KR | 10-2011-0134210 A | 12/2011 |
| KR | 10-2012-0043207 A | 5/2012 |
| KR | 10-2014-0037961 A | 3/2014 |
| RU | 2428430 C2 | 9/2009 |
| RU | 2519073 C1 | 6/2014 |
| RU | 2014117563 A | 12/2015 |
| TW | 200936154 | 9/2009 |
| TW | 201004649 A1 | 2/2010 |
| TW | 201204382 A1 | 2/2012 |
| WO | 96/32478 A1 | 10/1996 |
| WO | 97/34631 A1 | 9/1997 |
| WO | 02/046227 A3 | 6/2002 |
| WO | 2005/000892 A2 | 1/2005 |
| WO | 2005/047336 A1 | 5/2005 |
| WO | 2005/047337 A1 | 5/2005 |
| WO | 2006000448 A2 | 1/2006 |
| WO | 2006/068910 A1 | 6/2006 |
| WO | 2006/076471 A3 | 7/2006 |
| WO | 2007/012188 A1 | 2/2007 |
| WO | 2008/082274 A1 | 7/2008 |
| WO | 2009/011544 A2 | 1/2009 |
| WO | 2009020094 A1 | 2/2009 |
| WO | 2009/069983 A2 | 6/2009 |
| WO | 2009/099763 A1 | 8/2009 |
| WO | 2010/011096 A2 | 1/2010 |
| WO | 2010/080606 A1 | 7/2010 |
| WO | 2010107256 A2 | 9/2010 |
| WO | 2011/011073 | 1/2011 |
| WO | 2011/064758 A2 | 6/2011 |
| WO | 2011/122921 A2 | 10/2011 |
| WO | 2012/011752 A1 | 1/2012 |
| WO | 2012137479 A1 | 10/2012 |
| WO | 2012/165915 A2 | 12/2012 |
| WO | 2012/169798 A2 | 12/2012 |
| WO | 2012173422 A1 | 12/2012 |

(56) References Cited

FOREIGN PATENT DOCUMENTS

| WO | 2013/066106 A1 | 5/2013 |
|---|---|---|
| WO | 2013/100702 A1 | 7/2013 |
| WO | 2013100704 A1 | 7/2013 |
| WO | 2013/119903 A1 | 8/2013 |
| WO | 2013133659 A1 | 9/2013 |
| WO | 2014013262 A1 | 1/2014 |
| WO | 2014017845 A2 | 1/2014 |
| WO | 2014017849 A1 | 1/2014 |
| WO | 2014/133327 A1 | 9/2014 |
| WO | 2014/137161 A1 | 9/2014 |

OTHER PUBLICATIONS

Webber et al., Genes and homology, Current Biology, vol. 14(9):R:332-R333 (May 4, 2004) (Year: 2004).*
Rost, Twilight zone of protein sequence alignments, Protein Engineering, vol. 12(2):85-94 (1999). (Year: 1999).*
Hermanson (Chapter 18: Discrete PEG Reagents, Bioconjugate Techniques 2nd Ed., Peirce Biotechnology, ISBN: 978-0-12-370501-3, pp. 707-742, (2008) (Year: 2008).*
Eizo Sada et al., Resistance to Proteolysis of Antibody Ligands Modified with Polyethylene Glycol, Journal of Fermentation and Bioengineering, 1991, pp. 137-139, vol. 71, No. 2.
International Searching Authority, International Search Report for PCT/KR2012/009186 dated Mar. 28, 2013.
Korean Intellectual Property Office, Communication dated Feb. 3, 2016, issued in corresponding Korean application No. 10-2011-0114828.
European Patent Office, communication dated Feb. 17, 2015 issued in corresponding European application No. 12845690.2.
Chinese Intellectual Property Office, communication dated May 14, 2015 issued in corresponding Chinese application No. 201280054295.X.
State Intellectual Property Office of the P.R.C., Communication dated Nov. 12, 2015, issued in corresponding Chinese Application No. 201280054295.X.
Communication dated Aug. 29, 2016 by the Japanese Patent Office in corresponding Japanese Patent Application No. 2014-539876.
Hazra et al., Biotechnology Progress, 2010, No. 26, No. 6, pp. 1695-1704.
Mitchell, et al., "Targeting Primary Human Ph+ B-Cell Precursor Leukemia-Engrafted SCID Mice Using Radiolabeled Anti-CD19 Monoclonal Antibodies", The Journal of Nuclear Medicine, 2003, vol. 44, pp. 1105-11112 (9 pages).
Cunningham-Rundles, et al., "Biological activities of polyethyleneglycol immunoglobulin conjugates", Journal of Immunological Methods, vol. 152, 1992, pp. 177-190 (14 pages).
Russian Patent Office: Communication dated Sep. 27, 2016 in counterpart application No. 2014117563/10(027801).
Malaysian Patent Office; Communication dated Jun. 15, 2017 in counterpart application No. PI 2014001177.
Korean Patent Office; Communication dated Feb. 15, 2019 in application No. 10-2018-0018494.
Application documents for RU 2015133462.
Application documents for RU 2015139510.
Brazilian Patent Office, Communication dated Oct. 22, 2019, issued in application No. BR112014022187-1.
Dinesen et al., "Targeting nanomedicines in the treatment of Crohn's disease: focus on certolizumab pegol (CDP870)", International Journal of Nanomedicine, vol. 2, No. 1, pp. 39-47, 2007.
European Patent Office; Communication dated Nov. 12, 2015 in application No. 13757904.1.
International Searching Authority International Preliminary Report on Patentability dated Sep. 9, 2014 in International Application No. PCT/KR2013/001885.
International Searching Authority International Search Report for PCT/KR2013/001885 dated Jun. 25, 2013.
International Searching Authority Written Opinion for PCT/KR2013/001885 dated Jun. 25, 2013.
Korean Intellectual Property Office; Communication dated Aug. 23, 2016 in application No. 10-2013-0025344.
Korean Intellectual Property Office; Communication dated Dec. 4, 2015 in application No. 10-2013-0025344.
Russian Patent Office; Communication dated Dec. 19, 2016 in application No. 2014138621/10.
Taiwan Patent Office; Examination Report dated Jul. 19, 2017 in Taiwanese Patent Application No. 102108193.
The State Intellectual Property Office of P.R.C., Communication dated May 17, 2016, issued in counterpart Chinese Application No. 201380023673.2.
Ton et al., "Phase I Evaluation of CDP791, a PEGylated Di-Fab' Conjugate that Binds Vascular Endothelial Growth Factor Receptor 2", Clinical Cancer Research, vol. 13, No. 23, pp. 7113-7118, 2007.
Japan Patent Office; Communication dated Feb. 1, 2017 in JP Application No. 2014-560857.
Amit Chaudhary et al. "Enhancement of solubilization and bioavailability of poorly soluble drugs by physical and chemical modifications: A recent review", Journal of Advanced Pharmacy Education & Research, 2012, pp. 32-67, vol. 2, No. 1.
Bell et al., "To fuse or not to fuse: What is your purpose?", Protein Science, 2013, vol. 22, pp. 1466-1477 (12 pages total).
Chang Ki Lim et al., "Pharmacological Benefits of Once Weekly Combination Treatment using LAPS-Insulin and LAPS-Exendin-4 in Animal Models", Diabetes, Jul. 1, 2013, vol. 62, 950-P, XP055455455, p. A242.
Communication dated Mar. 21, 2018 from the European Patent Office in Application No. 15772562.3.
Communication dated Nov. 2, 2017 from the European Patent Office in European application No. 15772562.3.
Communication issued Dec. 2, 2016 by the Hungarian Patent Office in Hungarian Application No. P 16 00621.
Communication issued Oct. 2, 2017 by the Hungarian Patent Office in Application No. P1600621/11.
Czajkowsky et al., "Fc-fusion proteins: new developments and future perspectives", EMBO Molecular Medicine, vol. 4, pp. 1015-1028 (2012) (14 pages total).
Flanagan, M., et al., "Soluble Fc Fusion Proteins for Biomedical Research", Methods in Molecular Biology 378, 2007, 17 pages.
International Search Report of PCT/KR2015/003195 dated Jun. 18, 2015.
Japanese Patent Office; Communication dated Nov. 22, 2018 in application No. 2016-560523.
Meier, P., et al.," Soluble Dimeric Prion Protein Binds PrPsc In Vivo and Antagonizes Prion Disease", Cell, vol. 113, No. 1, 2003, p. 49-60 (12 pages).
Paul J Carter, "Introduction to current and future protein therapeutics: A protein engineering perspective", Experimental Cell Research, Elsevier, Feb. 2011, vol. 317, No. 9, XP028205664, pp. 1261-1269 (total 9 pages).
Young Jin Park et al., "Pharmacokinetics and Pharmacodynamics of Ultra-Long Acting Insulin (LAPS-Insulin) in Animal Models", Diabetes, Jun. 1, 2012, vol. 61, 919-P, XP055455447, p. A234.
Bandela et al., "Advanced peglyation for the development of raloxifene hydrochloride, bcs class ii drug", J Young Pharm (2009) 1(4) p. 295-300.
Pasut, "Polymers for Protein Conjugation", Polymers, 2014, 6, pp. 160-178.
AAT Bioquest ®, Inc., "SMCC and SMCC Plus ™ Protein Crosslinkers", Product Technical Information Sheet, Jul. 2012, 3 pages total.
Yu-Ting Liu et al., "Synthesis and characterization of novel ternary deep eutectic solvents", Chinese Chemical Letters, 2014, vol. 25, Issue 01, pp. 104-106 (3 pages total).
PubChem entry for propylene glycol, https://pubchem.ncbi.nlm.nih.gov/compound/Propylene-glycol, retrieved Jun. 3, 2021 (75 pages).
Tianlei Ying et al., "Soluble Monomeric IgG1 Fc", The Journal of Biological Chemistry, 2012, vol. 287, No. 23, pp. 19399-19408 (10 pages total).
Vidarsson et al., "IgG subclasses and allotypes: from structure to effector functions", Frontiers in Immunology, Oct. 20, 2014, vol. 5, Article 520, pp. 1-17 (17 pages total).

(56) References Cited

OTHER PUBLICATIONS

Tianlei Ying et al., "Soluble Monomeric IgG1 Fc", The Journal of Biological Chemistry, Jun. 1, 2012, vol. 287, No. 23, pp. 19399-19408 (10 pages total).

* cited by examiner

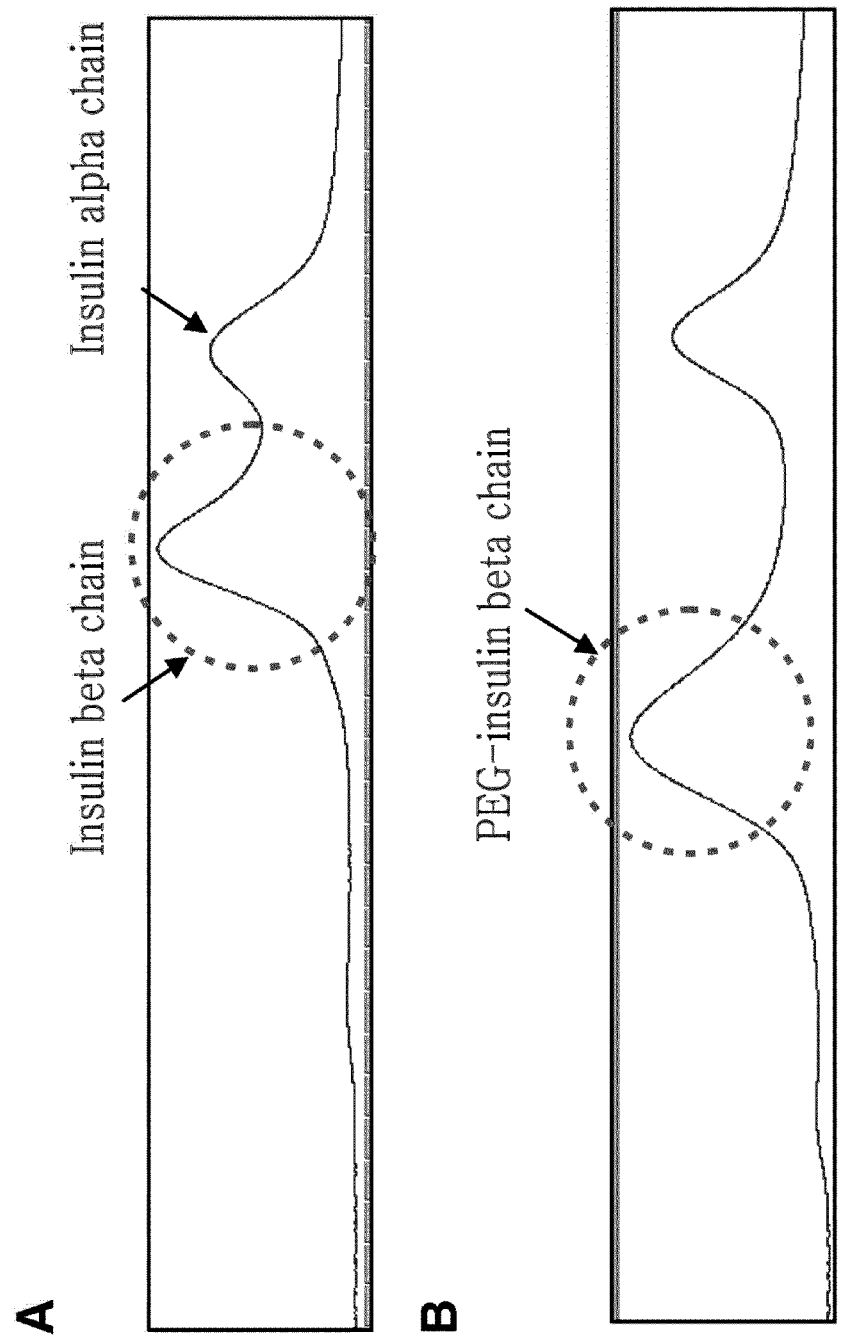
[Fig. 1]

[Figure 2]
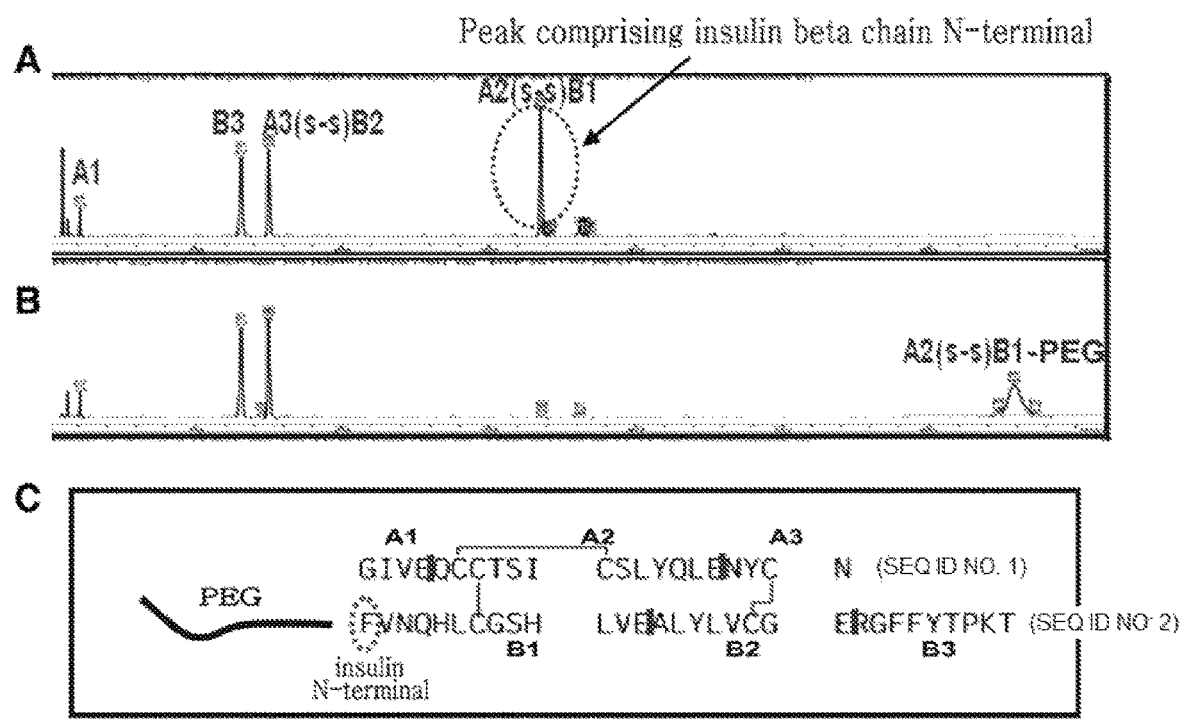

[Fig. 3]
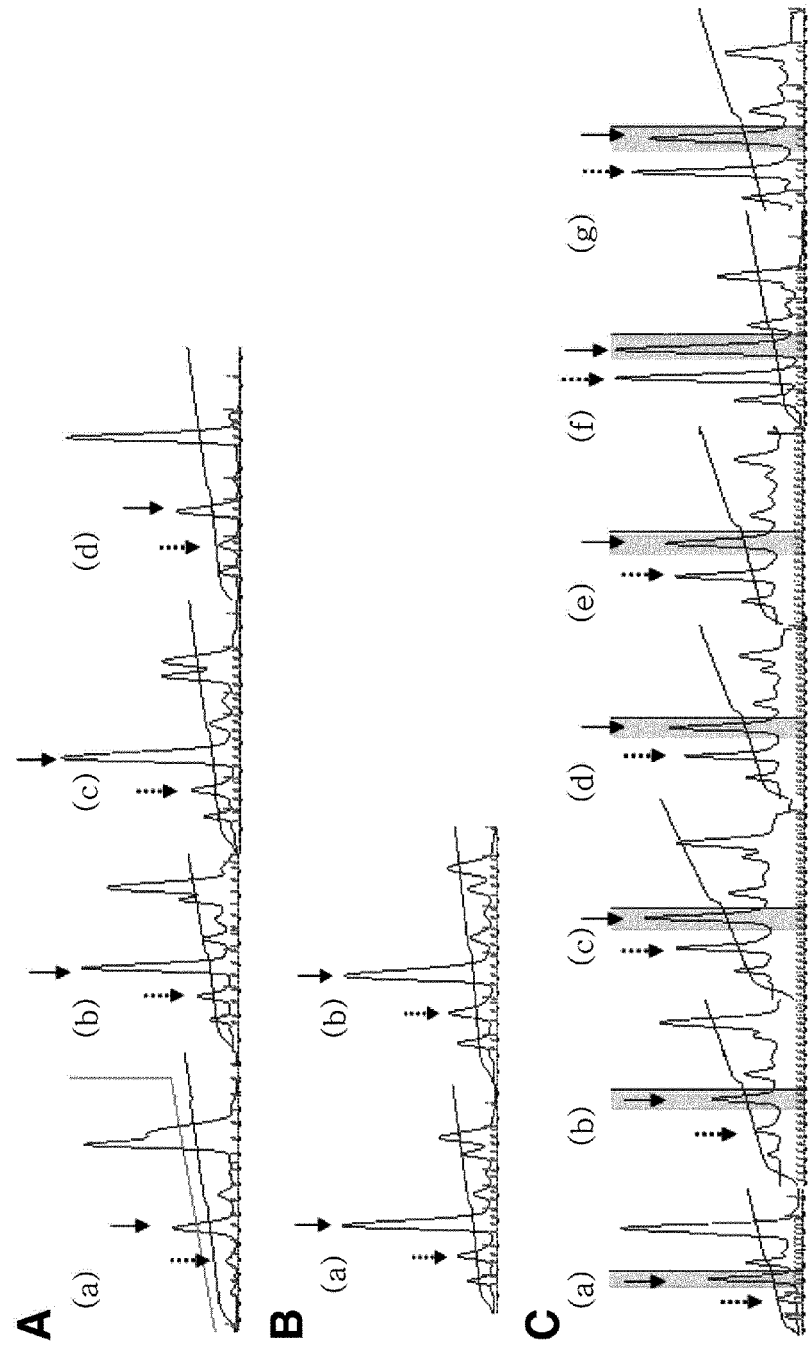

[Fig. 4]
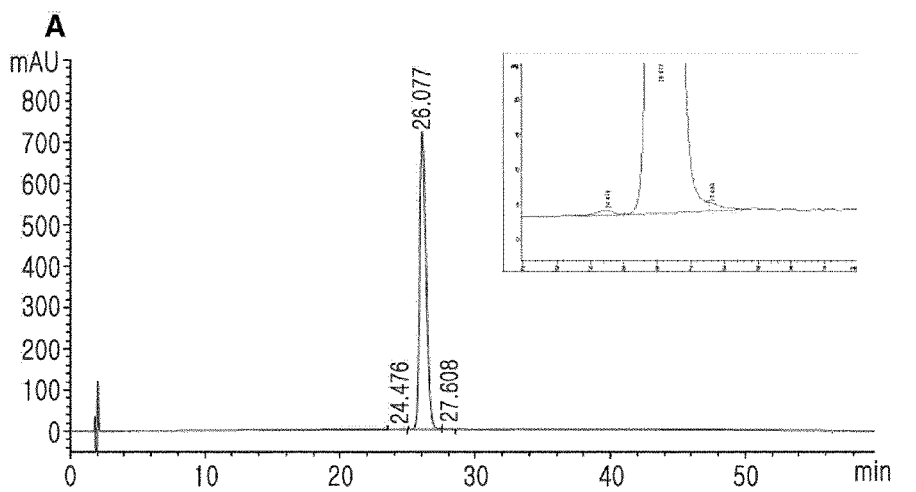
[Fig. 5]
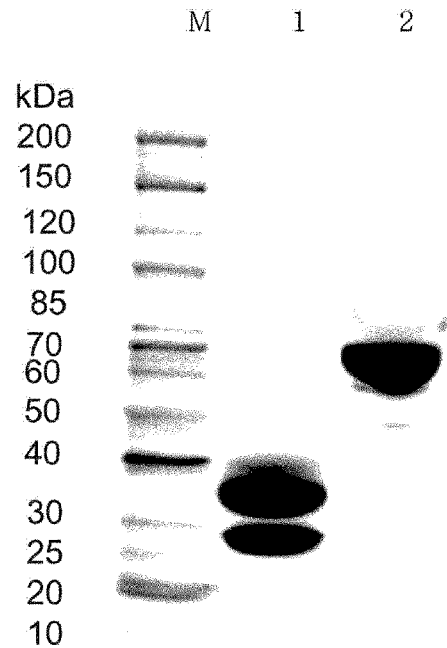

[Fig. 6]
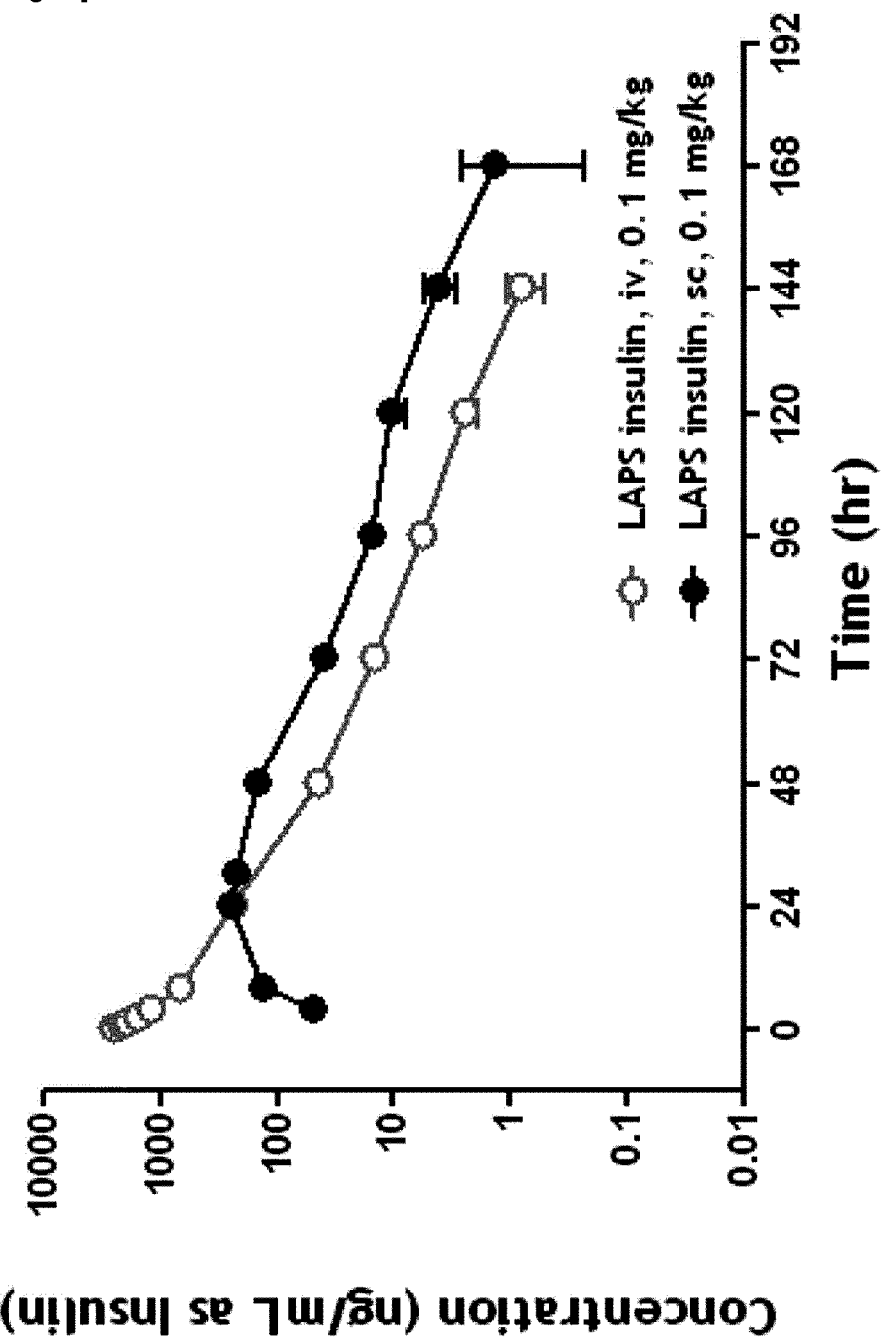

[Fig. 7]
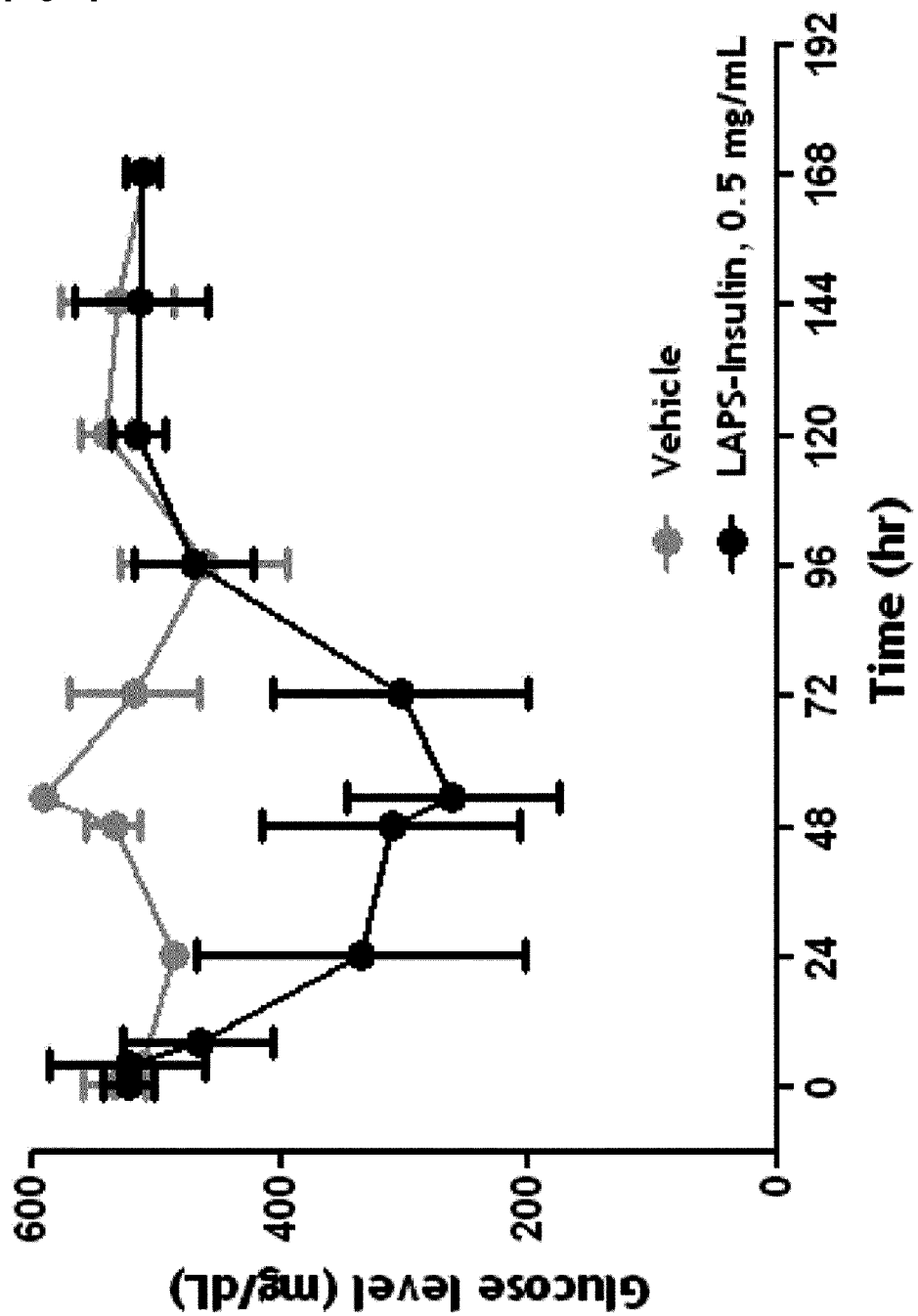

METHOD FOR PREPARING PHYSIOLOGICALLY ACTIVE POLYPEPTIDE COMPLEX

CROSS REFERENCE TO RELATED APPLICATIONS

This application is a National Stage of International Application No. PCT/KR2012/009186 filed Nov. 2, 2012, claiming priority based on Korean Patent Application No. 10-2011-0114828, filed Nov. 4, 2011, the contents of all of which are incorporated herein by reference in their entirety.

TECHNICAL FIELD

The present invention relates to a method for preparing a conjugate of a physiologically active polypeptide and a non-peptide polymer by linking the physiologically active polypeptide with the non-peptide polymer through a covalent bond using an organic solvent, and for preparing a physiologically active polypeptide complex by linking the conjugate with a carrier in order to improve the in vivo duration and stability of the physiologically active polypeptide.

BACKGROUND ART

In general, physiologically active polypeptides are easy to denature owing to their low stability and are decomposed by protein hydrolase to be readily removed through the kidney or liver. Therefore, in order to maintain the blood concentration and potency of protein medicines comprising a physiologically active polypeptide as the pharmacological active ingredient, it is necessary to frequently administer the protein medicine to patients. However, in the case of protein medicines administered to patients primarily in the form of an injectable formulation, frequent injections to maintain the blood concentration of active polypeptides may cause excessive suffering in patients. To solve such problems, there has been constant effort to maximize pharmacological efficacy by increasing the blood stability of protein drugs and maintaining the blood drug concentration for a longer time. Such sustained development of formulations is required to increase the stability of protein drugs and at the same time maintain the potency of the drugs themselves at a sufficiently high level, as well as to cause no immune reaction in patients.

In the prior art, for stabilizing proteins and inhibiting contact with protein hydrolase and loss through kidney, a method for chemically adding polymers having a high solubility such as polyethylene glycol (hereinafter referred to as PEG) to the surface of protein drugs has been used. It has been known that PEGs are effective in stabilizing proteins and preventing the hydrolysis of proteins by non-specifically binding PEG to a specific site or various sites of the target protein to increase the solubility of the protein, and do not cause any adverse side effects (Sada et al., J. Fermentation Bioengineering 71: 137-139, 1991). However, although such PEG binding can increase protein stability, it has the consequences that the potency of the physiologically active polypeptide is significantly lowered and that the reactivity of PEG with proteins is lowered concurrent with increasing the molecular weight of PEG to reduce the binding yield. Thus, the present inventors have provided the conjugate formed by linking a physiologically active polypeptide and carrier with a non-peptide polymer. However, the demand for a method of preparing the conjugate with high yield and purity has increased, and the prior method for first conjugating a carrier with a non-peptide polymer has the disadvantage that it incurs great expense.

Meanwhile, insulin is a polypeptide secreted from the beta cells of human pancreas as a material which plays a very important role in controlling the blood glucose level in the body. In cases where insulin is not properly secreted or insulin as secreted does not properly act in the body, blood glucose in the body cannot be controlled and is increased, thereby inducing the state referred to as diabetes. The case as stated above is referred to as type 2 diabetes mellitus, and the case where insulin is not secreted from the pancreas to increase blood glucose is referred to as type 1 diabetes mellitus.

Type 2 diabetes mellitus is treated with an oral hypoglycemic agent comprising a chemical material as the main component, and in certain patients is also treated with insulin. On the other hand, treatment of type 1 diabetes mellitus necessarily requires the administration of insulin.

The insulin therapy as widely used at the present time is a method for administering insulin via injection before and after meals. However, such insulin therapy requires it be constantly administered three times daily, and therefore causes much suffering and inconvenience. In order to overcome such problems, various attempts have been made. One of them has been an attempt to deliver peptide drugs into the body by way of inhalation through oral or nasal cavities by increasing the biological membrane permeability of peptide drugs. However, such a method has a significantly lower delivery efficiency in the body as compared to injection, and therefore there are many difficulties as yet in maintaining the in vivo activity of peptide drugs in the required conditions.

Further, a method for delaying absorption after subcutaneous administration of excessive drugs has been attempted. According to this, a method for maintaining blood drug concentration through only a single administration daily has been presented. Some have been approved as a medicinal product (e.g. Lantus, Sanofi-aventis) and are administered to patients at the present time. The study to modify insulin with fatty acids to strengthen the binding of insulin polymer and to extend the duration through binding to albumin present at the site of administration and in blood has progressed, and drugs produced using such a method have been approved as medicinal products (Levemir, NovoNordisk). However, such methods have the side effect of causing a pain at the site of administration, and additionally the administration interval of a single injection daily still lays a significant burden on patients.

Further, an effort has been continuously made to maximize the effect of peptide drugs by increasing blood stability and maintaining blood drug concentration at a high level for long periods after absorption of peptide drugs into the body. Such sustained development of peptide formulations is required to raise the stability of peptide drugs and at the same time maintain the potency of the drugs themselves at a sufficiently high level, as well as not to induce an immune reaction in patients. Such formulations of peptide drugs have been produced by means of a method for chemically adding polymeric material having high solubility, such as polyethylene glycol (PEG), to the surface of peptides.

PEGs are effective in inhibiting the loss of peptide through kidneys and preventing hydrolysis by non-specific binding to specific site or various sites of the target peptide to increase the molecular weight of the peptide, and additionally do not cause any adverse side effects. For example, WO 2006/076471 describes that B-type natriuretic peptides (BNP), which lower the arterial blood pressure by activating the production of cGMP by binding to NPR-A and are therefore used as an agent for treating congestive heart failure, are conjugated with PEG to maintain the biological activity of such peptides. U.S. Pat. No. 6,924,264 discloses the method for increasing the in vivo duration by conjugating the lysine residue of Exendin-4 with PEG. However, such methods can extend the in vivo duration of peptide drugs by increasing the molecular weight of PEG, but have the problem of the potency of peptide drugs being significantly lowered and the reactivity of PEG with peptides being lowered, thereby causing a decrease of yield, as the molecular weight increases.

WO 02/46227 discloses the fusion protein of GLP-1 and Exendin-4 or analogs thereof with human serum albumin or immunoglobulin fragment (Fc) by means of recombinant genetic technology, and U.S. Pat. No. 6,756,480 discloses the fusion protein of parathyroid hormone (PTH) and its analog with Fc. The methods disclosed therein can overcome the problems of low pegylation yield and non-specificity, but have problems in that the increase of the blood half-life is not remarkably high, contrary to expectation and, in some cases, possesses low titer. In order to maximize the effect of increasing the blood half-life, various kinds of peptide linkers can also be used, but may have a possibility of inducing an immunological reaction. In addition, there are problems in that, in cases where peptides having disulfide bonds such as BNP are used, application is difficult due to high misfolding probability, and in cases where non-native amino acid residues are present, production is impossible in the form of a genetic recombinant.

DISCLOSURE

Technical Problem

The present inventors made an effort to discover a method for simultaneously maximizing an increase in blood half-life and maintaining in vivo activity of physiologically active polypeptides comprising insulin. As the result, they have found that, in cases where physiologically active polypeptides are first linked to non-peptide polymers in the reaction solution containing an organic solvent, production costs can be reduced and the conjugate of physiologically active polypeptides and non-peptide polymers can be prepared with high yield and purity, as well as identifying the fact that when physiologically active polypeptide complexes are prepared using such a conjugate, the in vivo activity of the conjugate is maintained at a high level and the efficacy of increasing blood half-life is improved to a superior degree as compared to the known inframe fusion method, thereby completing the present invention.

Technical Solution

An object of the present invention is to provide a method for preparing a conjugate of a physiologically active polypeptide and non-peptide polymer, in order to extend the blood half-life while maintaining the in vivo activity of the physiologically active polypeptide.

Another object of the present invention is to provide a method for preparing a physiologically active polypeptide complex by covalently linking a carrier with the conjugate of a physiologically active polypeptide and non-peptide polymer.

Advantageous Effects

The method of the present invention can prepare the conjugate of the physiologically active polypeptide and non-peptide polymer with high purity and yield, and the physiologically active polypeptide complex as prepared by taking advantage of this can provide a subsequent reduction in production costs, and an extension of in vivo activity at a relatively high level and significant increase in the blood half-life, and thus can be effectively used for the development of sustained-release formulations of physiologically active polypeptide which can increase a patient's capacity for the administration of the drug.

DESCRIPTION OF DRAWINGS

FIG. 1 shows the result of analysis to identify insulin-PEG conjugate modification on the beta chain by means of SEC HPLC. A: reduction conditions of insulin, B: reduction conditions of PEG-insulin.

FIG. 2 shows the result of analysis to identify insulin-PEG conjugate modification on No. 1 phenylalanine (B1F) of the beta chain by 95% or more, by means of peptide mapping. A: result of insulin peptide mapping, B: result of PEG-insulin peptide mapping, C: PEG-insulin sequence and estimated cleavage sites in peptide mapping.

FIG. 3 shows the results of RP-HPLC, SE-HPLC analysis for insulin-PEG conjugate under respective conditions of buffer solutions. The solid line arrow represents peaks for mono-pegylated insulin, and the dotted line arrow represents peaks for impurities pegylated in the form of a bridge. Respective conditions of buffer solutions are as follows.

A: (a) 100 mM Potassium phosphate (pH 6.0) buffer solution; (b) 100 mM Potassium phosphate (pH 6.0), 30% isopropanol buffer solution; (c) 100 mM Potassium phosphate (pH 6.0), 45% isopropanol buffer solution; (d) 100 mM Potassium phosphate (pH 6.0), 55% isopropanol buffer solution;

B: (a) 50 mM Sodium Citrate (pH 6.0), 45% isopropanol buffer solution; (b) 50 mM Sodium Citrate (pH 6.0), 55% isopropanol buffer solution;

C: (a) 50 mM Sodium acetate (pH 4.0) buffer solution; (b) 50 mM Sodium acetate (pH 4.0), 10% isopropanol buffer solution; (c) 50 mM Sodium acetate (pH 4.0), 20% isopropanol buffer solution; (d) 50 mM Sodium acetate (pH 4.0), 30% isopropanol buffer solution; (e) 50 mM Sodium acetate (pH 4.0), 40% isopropanol buffer solution; (f) 50 mM Sodium acetate (pH 4.0), 45% isopropanol buffer solution; (g) 50 mM Sodium acetate (pH 4.0), 50% isopropanol buffer solution.

FIG. 4 shows the results of RP HPLC analysis (A) and SE HPLC analysis (B) for insulin-PEG-immunoglobulin Fc complex.

FIG. 5 shows the results of SDS PAGE analysis for insulin-PEG-immunoglobulin Fc complex. M: size marker, 1: reduction conditions of insulin-PEG-immunoglobulin Fc complex, 2: non-reduction conditions of insulin-PEG-immunoglobulin Fc complex.

FIG. 6 shows the results of a pharmacokinetic test to identify the in vivo duration of insulin-PEG-immunoglobulin Fc complex. iv: intravenous administration, sc: subcutaneous administration.

FIG. 7 shows the results of the in vivo potency test for insulin-PEG-immunoglobulin Fc complex.

BEST MODE

In one aspect to achieve the above object, the present invention provides a method for preparing the conjugate of a physiologically active polypeptide and non-peptide polymer, comprising: (1) reacting the physiologically active polypeptide with the non-peptide polymer in the reaction solution comprising an organic solvent to link the physiologically active polypeptide with the non-peptide polymer; and (2) separating and purifying the conjugate of physiologically active polypeptides covalently bound to non-peptide polymers from the reaction mixture of step (1).

The organic solvent as used in the present invention denotes a liquid organic compound capable of dissolving solid, gas and liquid, and can be comprised in the reaction solution in order that non-peptide polymers can be covalently bound to N-terminal of physiologically active polypeptides with high yield and purity, for the purposes of the present invention.

Any organic solvents which are conventionally used in the art can be applied to the present invention. The organic solvent used in the present invention can preferably comprise, but is not limited to, all of primary, secondary and tertiary alcohols. Alcohols having 1 to 10 carbon atoms can be used. More preferably, the alcohol may be isopropanol, ethanol or methanol. Any suitable organic solvent can be freely selected, according to the kind of physiologically active polypeptide.

The organic solvents are contained in the reaction solution for linking between a physiologically active polypeptide and non-peptide polymer, and can be comprised of, but are not limited to, an amount of 10 to 60%, preferably in an amount of 30 to 55%, and more preferably in an amount of 45 to 55% by volume, on the basis of the total volume of the reaction solution. In addition, pH of the reaction solution can preferably be, but is not limited to, 4.5 to 7.0, and more preferably 5.5 to 6.5. In this case, although physiologically active polypeptides generally show a tendency to lower the solubility in the reaction solution having weak acid pH, use of the organic solvent according to the present invention has the advantage that said problem of solubility can be resolved to smoothly progress the reaction.

In one embodiment of the present invention, in order to conjugate PEG selectively to N-terminal of insulin beta chain, isopropanol as the organic solvent was comprised in the reaction solution to conduct the pegylation of insulin at various levels of pH. Then, it was found that in cases where the organic solvent is included in the reaction solution, various kinds of impurities can be efficiently reduced to prepare the conjugate of the physiologically active polypeptide and non-peptide polymer with high purity and yield (Table 1), and taking advantage of such a discovery, the uniform and highly purified physiologically active polypeptide complex can finally be prepared. In the embodiment of the present invention, the content of impurities and the ratio of mono-pegylated insulin can be varied with the content of isopropanol and the pH of the reaction solution. Particularly, it was identified that when isopropanol is contained at the level of 45 to 55% on the basis of the total amount of the reaction solution at pH 6.0, the content of mono-pegylated insulin reaches the maximum attainable level (Table 1).

The term "physiologically active polypeptide" as used in the present invention represents the general concept of polypeptides having any physiological function in living bodies, and has the common features having the structure of polypeptides and also has various physiological activities. The physiological activities play a role in correcting abnormal pathologies due to deficiency and excessive secretion of substances concerned in regulating the physiological functions in the living body by controlling the genetic presentation and physiological functions. The physiologically active polypeptide can comprise general protein therapeutics.

The physiologically active polypeptides as used in the present invention comprise all the substances having physiological activities in the living body without any limitation, and can comprise, for example, insulin, luteotrophic hormone (LTH), follicle-stimulating hormone (FSH), blood coagulation factor VIII, blood coagulation factor VII, adiponectin, antibody, antibody fragments scFv, Fab, Fab', F(ab')2, or relaxin, etc., preferably being insulin. The physiologically active polypeptides can have two or more N-terminals (amino terminals).

Insulin as used in the present invention is a peptide having the function of controlling blood sugar according to the mechanism that insulin is secreted from the pancreas under the condition where blood sugar in a body is high, and absorbs sugar in liver, muscle and adipose tissues to be stored as glycogen, and inhibits the decomposition of fat and its use as an energy source. Such peptides include insulin agonists, precursors, derivatives, fragments, variants, etc., preferably being native insulin, immediate-releasing insulin, sustained-releasing insulin.

The native insulin is a hormone secreted from pancreas, and generally plays a role in controlling blood sugar in the body by promoting the absorption of glucose in cells and inhibiting the decomposition of fat. Insulin is produced through a series of processes by way of proinsulin precursors having no function controlling blood sugar to insulin, having the function of controlling blood sugar. The amino acid sequence of insulin is as follows.

```
Alpha chain:
                                      (SEQ ID NO: 1)
Gly-Ile-Val-Glu-Gln-Cys-Cys-Thr-Ser-Ile-Cys-Ser- Leu-Tyr-Gln-Leu-Glu-Asn-Tyr-Cys-Asn Beta chain:
                                      (SEQ ID NO: 2)
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr
```

Insulin agonists mean the substance which is bound to the in vivo receptor of insulin exhibits the same biological activities as insulin regardless of the structure of insulin.

Insulin derivatives denote a peptide which shows a sequence homology of at least 80% in an amino acid sequence as compared to native insulin, has some groups of amino acid residues altered in the form of chemical substitution (e.g. alpha-methylation, alpha-hydroxylation), removal (e.g. deamination) or modification (e.g. N-methylation, glycosylation, fatty acid), and has a function of controlling blood sugar in the body.

Insulin fragments denote the type of insulin wherein one or more amino acids are added to, or deleted from, amino or carboxy terminals of insulin, and the amino acids as added can also be non-native amino acids (e.g. amino acid type D). Such insulin fragments retain the function of controlling blood sugar in the body.

Insulin variants denote a peptide which differs from insulin in one ore more in the amino acid sequence, and retains the function of controlling blood sugar in the body.

The respective methods for preparation of insulin agonists, derivatives, fragments and variants can be used independently or in combination. For example, peptides of which one or more in the amino acid sequence differ from those of insulin and which have deamination at N-terminal amino acid residue and also have the function of controlling blood sugar in the body are included in the present invention.

As specific to one embodiment, insulin used in the present invention can be produced through the recombination method, and can also be produced from the synthetic method including solid phase synthesis.

Further, insulin used in the present invention can be characterized in that non-peptide polymer is conjugated with N-terminals (amino terminals) of beta chain. In case of insulin, since modification of alpha chain leads to decreased activities and a lowering of stability, the present invention can link a non-peptide polymer to beta chain N-terminal of insulin to maintain the activity of insulin while improving the stability of insulin.

The term "blood coagulation factor" as used in the present invention denotes the protein involved in blood coagulation which acts to protect the body through blood coagulation in cases where bleeding due to wounds occurs. Blood coagulation is a series of reactions which involve 12 factors. Among them, blood coagulation factor VIII also refers to antihemophilic factor, which is the factor raising hemophilia due to its genetic deficiency, and blood coagulation actor VII also refers to proconvertin and is the factor which can be used as the blood coagulator to cause blood coagulation through its activation.

The term "adiponectin" as used in the present invention denotes the protein secreted from adipose cells, and is the substance involved in the metabolism of fat and sugar. Adiponectin is the protein known as having the function of reducing a risks of heart disease and diabetes mellitus in the period of adulthood and inhibiting appetite by allowing muscles to convert fat into energy. In addition, the term "relaxin" denotes a hormone which is secreted from ovarian corpus luteum, and relaxes pubic symphysis and promotes childbirth. Relaxin is a hormone which plays a role in relaxing bones and joints in the entire body.

The term "non-peptide polymer" as used in the present invention denotes the biocompatible polymer formed by combining two or more repeating units, wherein the repeating units are linked with each other through optional covalent bond rather than peptide bond.

Non-peptide polymers which can be used in the present invention can be selected from the group consisting of polyethylene glycol, polypropylene glycol, copolymer of ethylene glycol and propylene glycol, polyoxyethylated polyol, polyvinyl alcohol, polysaccharide, dextran, polyvinyl ethyl ether, biodegradable polymers such as polylactic acid (PLA) and polylactic-glycolic acid (PLGA), lipid polymers, chitins, hyaluronic acid and the combination thereof, preferably being polyethylene glycol. All of the derivatives thereof already known in the art and the derivatives which can be readily prepared at the technical level of the art are included within the scope of the present invention.

Peptide linkers used in the fusion protein prepared according to the prior inframe fusion method have the disadvantage that they are easily cleaved in vivo by proteolytic enzymes, and therefore, any increase of the blood half-life of active drugs due to use of the corresponding carrier falls short of expectation. However, in the present invention the blood half-life of the peptide is found to be similar to that of the carrier, due to using polymers which are resistant to proteolytic enzymes. Therefore, in the present invention any polymer having said function, i.e. having a resistance to in vivo proteolytic enzyme can be used as the non-peptide polymer without any limitation. The non-peptide polymers have preferably a molecular weight in the range of 1 to 100 kDa, and preferably in the range of 1 to 20 kDa. In addition, although the non-peptide polymer to be conjugated with the physiologically active polypeptide may be one kind of polymer, the combination of different kinds of polymers can also be used in the present invention.

The non-peptide polymers as used in the present invention can have the reactive groups on both ends or three ends which can be conjugated with the physiologically active polypeptides and carriers.

The reactive groups of the non-peptide polymers can preferably be, but are not limited to, a reactive aldehyde group, propionaldehyde group, butyraldehyde group, maleimide group, ortho-pyridyl disulfide, and thiol or succinimide derivatives. In the above, the succinimide derivatives succinimidyl propionate, hydroxy succinimidyl, succinimidyl carboxymethyl or succinimidyl carbonate can also be used. Particularly, when the non-peptide polymers have reactive aldehyde groups as the reactive group on their ends, they are effective for minimizing non-specific reaction, and for conjugating the non-peptide polymers respectively with the physiologically active polypeptides and carriers on their ends. The final products produced from reductive alkylation with aldehyde bonds are far more stable than those produced from the linking with amide bonds. Aldehyde reactive groups can be selectively reacted with amino terminals at low pH level, and can form the covalent bond with lysine residues at high pH level, for example, under the condition of pH 9.0.

The reactive groups present on both ends or three ends of the non-peptide polymers can be identical to, or different from, each other. For example, a maleimide group can be present on one end, and an aldehyde group, propionaldehyde group or butyraldehyde group can be present on the other end. When poly(ethylene glycol) having hydroxy reactive groups on both ends is used as the non-peptide polymer, the protein conjugate of the present invention can be prepared by activating the hydroxy groups into the various reactive groups with known chemical reactions or by using commercially available poly(ethylene glycols) having modified reactive groups.

In the meantime, the procedure for separating and purifying the conjugate comprising physiologically active polypeptide of which N-terminals are covalently bound with non-peptide polymer, in the step (2) of the present invention can use any method known in the art without any limitation, and can preferably employ ion exchange chromatography.

In another aspect, the present invention provides a method for preparing physiologically active polypeptide complex, comprising (1) preparing the conjugate of physiologically active polypeptide and non-peptide polymer according to said method; and (2) covalently linking a carrier selected from the group consisting of immunoglobulin Fc region, antibody, albumin and transferrin with the non-peptide polymer of the conjugate to produce a peptide complex in which ends of non-peptide polymer are bound respectively to the physiologically active polypeptide and the carrier.

In the present invention, the "complex" is intended to refer to a structure composed of at least one physiologically active polypeptide, at least one non-peptidyl polymer and at least one carrier, with interconnection via covalent bonds among them. In order to differentiate itself from a "complex", the "conjugate" is used herein to refer to a structure in which only pairs of the physiologically active polypeptide and the non-peptide polymer are interconnected via a covalent bond.

In the present invention, the "carrier" denotes a substance to be bound to the drug, and generally a substance that is bound to the drug to either increase and decrease or remove the biological activities of the drug. For the purpose of the present invention, the drug to be bound to the carrier is preferably physiologically active polypeptides, which can also be bound to non-peptide polymers. The carrier is a substance to minimize a decrease in the in vivo activity of the physiologically active polypeptide to be bound and at the same time to increase the in vivo stability of the drug. The carrier can preferably comprise, but is not limited to, immunoglobulin Fc region, antibody, albumin and transferrin.

The immunoglobulin Fc region is a biodegradable polypeptide which is metabolized in the living body, and therefore, is safe in being used as the carrier for the drug. In addition, since immunoglobulin Fc region has a molecular weight smaller than that of a whole immunoglobulin molecule, it is advantageous in view of the preparation, purification and yield of the conjugate. Further, since amino acid sequences are different in every antibody, by removing Fab portions showing a high heterogeneity it can be expected to provide the effect that homogeneity of the substances can be greatly increased and the possibility of inducing the blood antigenicity is lowered.

In the present invention, the "immunoglobulin Fc region" denotes heavy chain constant region 2 (CH2) and heavy chain constant region 3 (CH3) portions of immunoglobulin, except for heavy and light chain variable regions, heavy chain constant region 1 (CH1) and light chain constant region 1 (CL1) of immunoglobulin, and can also comprise hinge portion in heavy chain constant region. In addition, if the immunoglobulin Fc region of the present invention has a substantially equivalent or improved effect as compared to the native form, it can be the expanded Fc region comprising a part or whole of heavy chain constant region 1 (CH1) and/or light chain constant region 1 (CL1), except for heavy chain and light chain variable regions of immunoglobulin. Further, it can also be the region wherein significantly long amino acid sequences corresponding to CH2 and/or CH3 are removed. That is, the immunoglobulin Fc region of the present invention can be (1) CH1 domain, CH2 domain, CH3 domain and CH4 domain, (2) CH1 domain and CH2 domain, (3) CH1 domain and CH3 domain, (4) CH2 domain and CH3 domain, (5) the combination of one or two or more domains and the immunoglobulin hinge region (or a part of the hinge region), and (6) a dimer of respective domains of heavy chain constant regions and light constant regions.

Further, the immunoglobulin Fc region of the present invention includes native amino acid sequences as well as their sequence mutants. The mutants of amino acid sequence denote those having different sequences due to deletion, insertion, non-conservative or conservative substitution of one or more amino acid residues in the native amino acid sequence, and the combination thereof. For example, in case of IgG Fc, amino acid residues present in the positions of 214 to 238, 297 to 299, 318 to 322, or 327 to 331 can be used as sites suitable for modification. In addition, various kinds of mutants in which sites capable of forming disulfide bonds are removed, some amino acids are removed from N-terminals of native Fc, or methionine residues can also be added to N-terminals of native Fc are available. Further, in order to remove the effector function complement binding sites, for example, Clq binding sites can be removed, and ADCC sites can also be removed. The techniques for preparing such sequence mutants of immunoglobulin Fc region have been disclosed in International Patent Publication No. 97/34631, and International Patent Publication No. 96/32478, among others.

Some of the exchange of amino acids in proteins and peptides which does not totally alter the activities of molecules has been done in the art (H. Neurath, R. L. Hill, The Proteins, Academic Press, New York, 1979). The most commonly occurring exchange is the exchange between amino acid residues Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, or Asp/Gly.

If appropriate, they can be modified with phosphorylation, sulfation, acrylation, glycosylation, methylation, farnesylation, acetylation, amidation, etc.

Fc mutants as described above are mutants which show the same biological activities as the Fc region of the present invention, and furthermore have the enhanced structural stability of the Fc region against heat, pH, etc.

Further, such an Fc region can be obtained from the native form separated from the living body of human, and animals including cattle, goats, pigs, mice, rabbits, hamsters, rats, guinea pigs, etc., can also be the recombinants obtained from transformed animal cells or microorganisms, or the derivatives thereof. Herein, Fc regions acquired from the native form can be obtained by separating the whole immunoglobulin from the living body of human or animals, and treating the whole immunoglobulin with proteolytic enzymes. When immunoglobulin is treated with papain, it is cleaved into Fab and Fc, and in case of pepsin treatment immunoglobulin can be cleaved into pF'c and F(ab)2. Then, the reaction mixture can be subjected to size-exclusion chromatography to separate Fc or pF'c.

Preferable is the recombinant immunoglobulin Fc region obtained from human-derived Fc region using microorganisms.

Further, the immunoglobulin Fc region can be in forms which have a native glycosyl chain, which increase the glycosyl chain as compared to native form, decrease the glycosyl chain as compared to native form, or are deglycosylated. The increase and decrease, or removal of such immunoglobulin Fc glycosyl chains can be accomplished by means of conventional methods including chemical methods, enzymological methods, and genetic engineering methods using microorganisms. Herein, since immunoglobulin Fc regions in which the glycosyl chain is removed fromFc show a significant lowering of binding force of the complement (clq), and provide a decrease or removal of antibody-dependent cytotoxicity or complement-dependent cytotoxicity, they do not induce any necessary immune reactions in the living body. In view of this, the form which is more suitable for the essential purpose of the present invention as the carrier for the drugs may be deglycosylated or aglycosylated immunoglobulin Fc region.

In the present invention, the "deglycosylation" refers to the Fc region from which glycosyl group is removed with enzymes, and "aglycosylation" denotes Fc region which is produced from prokaryotic animals, preferably from E. coli, and is not glycosylated.

In addition, the immunoglobulin Fc region can be the Fc region derived from IgG, IgA, IgD, IgE, or IgM, or Fc region derived from their combination or a hybrid therein. Preferably, the immunoglobulin Fc region can be derived from IgG or IgM, which are most abundant in human blood, and is most preferably derived from IgG known to improve the half-life of ligand-conjugated proteins.

Meanwhile, the "combination" in the present invention denotes that a binding of polypeptides encoding for single-chain immunoglobulin Fc region derived from the same origin with single-chain polypeptides derived from a different origin is formed in the production of the dimers or multimers. That is, it is possible to prepare the dimers or multimers from two or more fragments selected from the group consisting of IgG Fc, IgA Fc, IgM Fc, IgD Fc and IgE Fc fragments.

In the present invention, the term "hybrid" denotes that the sequences corresponding to two or more immunoglobulin Fc fragments derived from different origins are present in the single-chain immunoglobulin Fc region. In the specific embodiment of the present invention, various types of hybrids are available. That is, hybrids comprising one to four domains selected from the group consisting of CH1, CH2, CH3 and CH4 of IgG Fc, IgM Fc, IgA Fc, IgE Fc and IgD Fc are available, which can further comprise the hinge portion.

Further, IgG can also be classified into subclasses of IgG1, IgG2, IgG3 and IgG4, and in the present invention the combination or hydride thereof can also be used. IgG2 and IgG4 subclasses are preferable, and the Fc region of IgG4 which has practically no effector function, such as complement-dependent cytotoxicity (CDC), is most preferable.

That is, the immunoglobulin Fc region most preferably used as the carrier for the drug which is in the present invention is human IgG4-derived aglycosylated Fc domain. Human-derived Fc regions act as an antigen in the human body, and therefore, are more preferable than non-human-derived Fc regions, which may cause undesirable immune reactions such as a formation of a new antibody.

The physiologically active polypeptide complex of the present invention can be prepared with high purity and yield according to the method of the present invention, and can show improved in vivo duration and stability so that an adaptability of taking medicine can be improved by far in treatment with physiologically active polypeptide. In one example of the present invention, insulin-PEG-immunoglobulin Fc complexes prepared according to the method of the present invention were used to confirm their in vivo elimination half-life. As a result, we have identified that they showed a duration of 15.73 hours in case of intravenous administration and 16.98 hours in case of subcutaneous administration, which is 30 times longer than a duration of about 0.5 hours in the case of native insulin (FIG. 6). Further, as per the result of in vivo potency test, we have also found that their blood sugar lowering potency lasts for approximately 4 days (FIG. 7).

The present invention can also provide a sustained formulation of physiologically active polypeptides comprising the physiologically active polypeptide complexes.

In the present invention, the term "administration" means that a given substance is introduced into a patient by means of any suitable method. The complexes can be administered through any of the conventional routes as long as the route can allow the drug to reach the target tissue. The administration of the complex can include, but is not limited to, intraperitoneal, intravenous, intramuscular, subcutaneous, intradermal, oral, topical, intranasal, intrapulmonary, intrarectal administration, and the like. However, since peptide drugs are digested in the case of oral administration, it is preferable that the oral composition is formulated by coating the active drug so as to be protected from gastric digestion. Preferably, the complexes of the present invention can be administered in the form of an injection. In addition, the sustained-release formulation can be administered by means of any optional apparatus which can allow the active material to move to the target cells.

The sustained-release formulation comprising the complex of the present invention can comprise a pharmaceutically acceptable carrier. Pharmaceutically acceptable carriers include binders, lubricants, disintegrants, excipients, solubilizers, dispersants, stabilizers, suspending agents, colorants, perfumes, etc. that can be used for oral administration; buffers, preservatives, agents for painlessness, solubilizers, agents for isotonicity, stabilizers, etc. can be used in their combination for injections; and bases, excipients, lubricants, preservatives, etc. can be used for topical administration. The sustained-release formulation of the present invention can be diversely prepared by having been mixed together with the pharmaceutically acceptable carriers as described above. For example, the formulation can be prepared in the form of tablets, troches, capsules, elixirs, suspensions, syrups, wafers, etc. for oral administration, and in the form of ampoules for unit or multiple dosing for injection. The complexes of the present invention can also be formulated in other forms including solutions, suspensions, tablets, pills, capsules, sustained-release formulations, etc.

Meanwhile, as examples of carriers, excipients and diluents suitable for formulation lactose, dextrose, sucrose, sorbitol, mannitol, xylitol, erythritol, maltitol, starch, acacia, alginate, gelatin, calcium phosphate, calcium silicate, cellulose, methyl cellulose, microcrystalline cellulose, polyvinylpyrrolidone, water, methyl hydroxy benzoate, propyl hydroxy benzoate, talc, magnesium stearate or mineral oils, etc. can be used. In addition, filler, anti-coagulants, lubricants, wetting agents, perfumes, preservatives, etc, can be additionally utilized.

The administration of the sustained-release formulation of the present invention can be determined depending on the kind of drugs used as the active ingredient, together with various factors concerned, including diseases to be treated, administration routes, age, sex and weight of patients, and severity of diseases, etc. The sustained-release formulations of the present invention have good in vivo duration and potency, and therefore, can lead to a significant decrease in the frequency of administration of the pharmaceutical formulation of the present invention. Further, the sustained-release formulation can maintain the in vivo duration and stability of physiologically active polypeptides, and therefore, can be effectively used for the treatment of diseases.

MODE FOR INVENTION

Hereinafter, it is intended to more specifically explain the present invention through Examples. However, these Examples are provided only to illustrate the present invention in greater detail and the scope of the present invention is not limited in any respect by these Examples.

Example 1

PEGylation Reaction of Insulin and Purification of Mono-Pegylated Insulin

Insulin powder was dissolved in 10 mM HCl, and then reacted with 3.4K propion-ALD2 PEG (PEG having two propionaldehyde groups, IDB, Korea) at 4~8° C. for about 2 hours under conditions including a molar ratio of 1:2-4 of insulin:PEG and insulin concentration of 3-5 mg/ml to pegylate the N-terminal of the insulin beta chain. This reaction was conducted under 50 mM sodium citrate pH 6.0, 45% isopropanol with addition of 4-20 mM NaCNBH$_3$ reductant. The reaction solution was purified with SP-HP (GE Healthcare) column using a buffer containing sodium citrate (pH 3.0) and 45% EtOH, and KCl concentration gradient.

It was identified through SE-HPLC and peptide mapping analysis that mono-PEGylated insulin thus prepared was pegylated by 98% or more on No. 1 phenylalanine (B1F) of beta chain (FIGS. 1 and 2).

Example 2

Change in the Yield and Impurity Content of Mono PEG-Insulin Depending on pH of the Reaction Solution and Concentration of the Organic Solvent To compare the reaction yield of mono PEG-insulin and the production of impurities during the preparation when such organic solvents such as isopropanol are included in the reaction solution for reaction insulin with PEG, insulin and 3.4K Propion-ALD2 PEG were reacted in a molar ratio of 1:2 with 3 mg/d of insulin concentration at 4° C. for 4 hours. Herein, as the reaction solution 50 mM sodium citrate pH 6.0, 45% isopropanol buffer solution; 50 mM sodium citrate pH 6.0, 55% isopropanol buffer solution; 100 mM potassium phosphate pH 6.0 buffer solution; 100 mM potassium phosphate pH 6.0, 30% isopropanol buffer solution; 100 mM potassium phosphate pH 6.0, 45% isopropanol buffer solution; 100 mM potassium phosphate pH 6.0, 55% isopropanol buffer solution; 50 mM sodium acetate pH 4.0 buffer solution; 50 mM sodium acetate pH 4.0, 10% isopropanol buffer solution; 50 mM sodium acetate pH 4.0, 20% isopropanol buffer solution; 50 mM sodium acetate pH 4.0, 30% isopropanol buffer solution; 50 mM sodium acetate pH 4.0, 40% isopropanol buffer solution; sodium acetate pH 4.0, 45% isopropanol buffer solution; and 50 mM sodium acetate pH 4.0, 50% isopropanol buffer solution were respectively used, to which 20 mM NaCNBH$_3$ was added as the reductant. Respective reaction solutions were purified with the same method as used in Example 1, and the purification profiles thereof are shown in FIG. 3. When both N-terminals of alpha and beta chains of insulin are simultaneously reacted with PEG in the form of a bridge, it is impossible for a coupling reaction of mono-pegylated insulin with immunoglobulin Fc to occur. Thus, the ratio of such impurities is shown in Table 1. As seen from Table 1, it was identified that the ratio of mono-pegylated insulin is varied with the content of isopropanol in the reaction solution and pH condition, and the content of mono-pegylated insulin reaches the maximum at pH 6.0 when the content of isopropanol is about 45~55%. Low pH condition led to the consequence of an increase in the content of bridge-type pegylated impurities as the content of isopropanol is elevated, and thereby caused a decrease in the yield of mono-pegylated insulin.

TABLE 1

| Buffer condition | Organic solvent | Content of bridge-type pegylated impurities | Content of mono PEG-insulin |
|---|---|---|---|
| 100 mM Potassium phosphate (pH 6.0) | — | 1.9% | 12.0% |
| | 30% isopropanol | 8.1% | 32.0% |
| | 45% isopropanol | 10.5% | 44.0% |
| | 55% isopropanol | 6.4% | 21.0% |
| 50 mM Sodium Citrate (pH 6.0) | 45% isopropanol | 9.9% | 45.0% |
| | 55% isopropanol | 12.3% | 43.0% |

TABLE 1-continued

| Buffer condition | Organic solvent | Content of bridge-type pegylated impurities | Content of mono PEG-insulin |
|---|---|---|---|
| 50 mM Sodium acetate (pH 4.0), 0.2M NaCl | — | 4.7% | 18.0% |
| | 10% isopropanol | 6.9% | 18.0% |
| | 20% isopropanol | 19.3% | 27.0% |
| | 30% isopropanol | 25.7% | 31.0% |
| | 40% isopropanol | 28.9% | 32.0% |
| | 45% isopropanol | 31.0% | 34.0% |
| | 50% isopropanol | 33.9% | 34.0% |

Example 3

Preparation of the Complex of Mono-Pegylated Insulin and Immunoglobulin Fc

To prepare the insulin-PEG-immunoglobulin Fc complex, mono-pegylated insulin as prepared by the method of Example 1 and immunoglobulin Fc were reacted in the molar ratio of 1:1 with a total protein level of 20-50 mg/ml, at 25° C. for 15-17 hours. In this reaction, the reaction solution included 100 mM HEPES, 22 mM potassium phosphate, 10% ethanol, pH8.2, and further contained 20 mM NaCNBH$_3$ as the reductant.

After completion of the reaction, the reaction solution was first purified through Source 15Q (GE Healthcare) column to remove any residual immunoglobulin Fc and mono-pegylated insulin. In this case, the elution was conducted using Tris-HCl (pH 7.5) buffer and NaCl concentration gradient.

Then, Source 15ISO (GE Healthcare) was used as the second column to remove any residual complex of immunoglobulin Fc and multi-pegylated insulin, thereby obtaining the insulin-PEG-immunoglobulin Fc complex. In this case, the elution was conducted using the concentration gradient of ammonium sulfate comprising Tris-HCl (pH 7.5).

The eluted insulin-PEG-immunoglobulin Fc complex was analyzed with RP-HPLC, SE-HPLC and SDS PAGE, and then confirmed to have been prepared with a high purity of at least 98% (FIGS. 4 and 5).

Example 4

Measuring the In Vivo Elimination Half-Life of Sustained-Release Insulin Complex To confirm the in vivo duration of sustained-release insulin complex in the form of insulin-PEG-immunoglobulin Fc complex prepared in Example 3, normal male rat (Normal SD rat) was used to determine the pharmacokinetic profile of the drug as administered through intravenous and subcutaneous routes. 0.1 mg/kg (based on insulin) of the sustained-release insulin complex was intravenously and subcutaneously administered one time to a normal male rat, and then the change in blood concentration over time was measured by means of an insulin ELISA kit. From the values as measured, the pharmacokinetic parameters were computed using WinNonlin 5.2. As a result, it was identified that the in vivo elimination half-life of the sustained-release insulin complex was 15.73 hours in case of intravenous administration and 16.98 hours in case of subcutaneous administration, which correspond to the duration 30 times longer than about 0.5 hours in case of native insulin. Further, it was also identified that in case of subcutaneous administration the biological availability was about 54% (FIG. 6).

Example 5

In Vivo Potency Test for Insulin Complex

To compare the in vivo potency of the insulin complexes, the test for comparing the potency of lowering blood sugar was conducted in rats having streptozotocin-induced diabetes mellitus. Diabetes mellitus was induced by intraperitoneally administering streptozotocin dissolved in 10 mM citric acid buffer solution (pH 4.5) at the level of 60 mg/kg to normal rats that had been fasted for 16 hours. Then, the insulin complex was subcutaneously administered one time at the dose of 0.5 mg/kg to rats having blood sugar level raided to 500 mg/60 or more, and then the blood sugar lowering potency was compared. As a result, the blood sugar lowering effect of the insulin complex was observed to last for about 4 days and the blood sugar increased to a level equivalent to that of the vehicle on the $5^{th}$ day (FIG. 7).

lin molecule, wherein one of the aldehyde groups of the non-peptide polymer is covalently bound to the N-terminal of beta chain of the insulin, and remainder of the aldehyde groups of the non-peptide polymer of the conjugate is unbound, wherein the N-terminal of beta chain of the insulin is phenylalanine, wherein the reaction solution comprises the organic solvent in an amount of 45 to 55% by volume, based on the total volume of the reaction solution;

the organic solvent is selected from the group consisting of isopropanol, ethanol and methanol;

the non-peptide polymer is polyethylene glycol; and the reaction solution has a pH of 4.5 to 6.0 and comprises sodium citrate; and (2) covalently linking an immunoglobulin Fc region to the remainder aldehyde group of the non-peptide polymer of the conjugate of step (1) at a 1:1 ratio, in a reaction solution comprising 10% (v/v) ethanol, HEPES (4-(2-hydroxyethyl)-1-piperazineethanesulfonic acid), potassium phosphate, and 20 mM $NaCNBH_3$ and having pH 8.2 at 25° C. for 15-17 hours, to produce the insulin complex, in which ends of the non-peptide polymer are bound to the insulin and to the immunoglobulin Fc region, respectively.

---

---

The invention claimed is:

1. A method for preparing an insulin complex, comprising:
   (1) preparing a conjugate of an insulin having two N-terminals and a non-peptide polymer having aldehyde groups on both ends, comprising:
      (a) reacting the insulin with the non-peptide polymer in a reaction solution comprising an organic solvent to link the non-peptide polymer to N-terminal of beta chain of the insulin, thereby preparing the conjugate of the insulin and the non-peptide polymer, and
      (b) isolating and purifying the conjugate from a reaction mixture of the step (a), said conjugate consisting of one non-peptide polymer molecule and one insu- 2. The method according to claim 1, wherein the immunoglobulin Fc region is composed of 1 to 4 domains selected from the group consisting of CH1, CH2, CH3 and CH4 domains.

3. The method according to claim 1, wherein the immunoglobulin Fc region further comprises a hinge region.

4. The method according to claim 1, wherein the immunoglobulin Fc region is an Fc region derived from IgG, IgA, IgD, IgE or IgM.

5. The method according to claim 1, wherein the immunoglobulin Fc region is an IgG4 Fc region.

6. The method according to claim 1, wherein the immunoglobulin Fc region is a human aglycosylated IgG4 Fc region.

7. The method according to claim 1, wherein the organic solvent is isopropanol.

8. The method according to claim 1, wherein the aldehyde group is a propionaldehyde group or butyraldehyde group.

9. The method according to claim 1, wherein the isolation and purification are accomplished by ion exchange chromatography.

\* \* \* \* \*

SEQUENCE LISTING

```
<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```